US009199905B2

(12) United States Patent
Jackson et al.

(10) Patent No.: US 9,199,905 B2
(45) Date of Patent: Dec. 1, 2015

(54) PURE CARBOXYLIC ACID FILTRATION

(75) Inventors: Christopher H. Jackson, Stockton-on-Tees Cleveland (GB); Anthony Peter John Limbach, Sowerby Thirsk (GB); Finbar Gerald McDonnell, Guisborough Cleveland (GB); Alan MacPeherson Ure, Stockton-on-Tees Cleveland (GB)

(73) Assignee: INVISTA North America S.a.r.l., Wilmington, DE (US)

( * ) Notice: Subject to any disclaimer, the term of this patent is extended or adjusted under 35 U.S.C. 154(b) by 795 days.

(21) Appl. No.: 13/126,640

(22) PCT Filed: Oct. 30, 2009

(86) PCT No.: PCT/GB2009/002582
§ 371 (c)(1),
(2), (4) Date: Jun. 8, 2011

(87) PCT Pub. No.: WO2010/049697
PCT Pub. Date: May 6, 2010

(65) Prior Publication Data
US 2011/0269991 A1    Nov. 3, 2011

Related U.S. Application Data

(60) Provisional application No. 61/110,141, filed on Oct. 31, 2008.

(51) Int. Cl.
C07C 51/265    (2006.01)
C07C 51/47    (2006.01)

(52) U.S. Cl.
CPC ............... *C07C 51/265* (2013.01); *C07C 51/47* (2013.01)

(58) Field of Classification Search
None
See application file for complete search history.

(56) References Cited

U.S. PATENT DOCUMENTS 5,583,254 A      12/1996  Turner et al.
2006/0264658 A1  11/2006  Parker et al.

FOREIGN PATENT DOCUMENTS

GB    825998    12/1959

*Primary Examiner* — Yevegeny Valenrod
(74) *Attorney, Agent, or Firm* — William J. Simmons

(57) ABSTRACT

The present invention relates to a process for production of pure terephthalic acid comprising: a) removing a mother liquor from a terephthalic acid through a filter with a gas, wherein the gas comprises steam at a concentration of least about 50% by volume; b) purifying the gas; and c) recycling the gas purified in step (b) back to step (a).

25 Claims, 5 Drawing Sheets

PURE CARBOXYLIC ACID FILTRATION

FIELD OF THE INVENTION

This invention relates to a process for producing a pure carboxylic acid, for example the separation of mother liquor from a terephthalic acid without the inclusion of impurities.

BACKGROUND OF THE INVENTION

Pure terephthalic acid (PTA) is produced by the oxidation of paraxylene to form a crude terephthalic acid. The crude terephthalic acid is separated from the oxidation process solvent and is then purified, for example by using hydrogenation and/or crystallization techniques, to form a PTA slurry in aqueous mother liquor. The PTA is typically then separated from aqueous mother liquor in a two stage process. The first stage of separation is typically carried out in decanter centrifuges or rotary filters at a pressure of greater than 3 bara and a temperature of greater than 140° C. The damp cake leaving the first stage of separation is re-slurried in hot water before the pressure is reduced. The PTA is then separated from this water at atmospheric pressure in a second stage of separation. This second stage of separation is typically achieved using decanter centrifuges or rotary filters. The water removed in the second stage can be used to slurry CTA at the front end of the purification process. The final PTA product typically contains less than 150 ppm (w/w) of the intermediate para-toluic acid.

The two stage separation process described above can be improved by using rotary filters that allow a cake washing step to be applied during the filter cycle and hence improve the removal of soluble impurities. Reduced cake moisture versus centrifuges can also be achieved using such filters. If sufficient wash efficiency is established in the rotary filter, then an acceptable product quality can be achieved using a single stage of separation. To achieve this, the separation must be performed at a pressure of greater than 3 bara and a pressure letdown device used to allow the PTA to be transferred from the pressurized filter system to the low pressure systems downstream. This method can reduce the capital cost of the process and the manufacturing cost of the PTA.

The majority of the rotary pressure filters commercially available for this duty use a gas to displace the aqueous mother liquor and/or washing liquor. Typically the casing of the rotary filter is pressurized with an inert gas which forms a pressure driving force for displacing liquid from the filter cake. Some of this gas passes through the cake and a mixture of gas and liquid is collected in the filter drum or filter cells, depending on the rotary filter design. Some rotary filter designs allow the gas and liquids collected from different parts of the filter to be collected separately, other designs collect all gas and liquids together.

A problem with using an inert gas to create the pressure driving force is the fact that as it passes through the cake it causes evaporative cooling and precipitation of impurities from the mother liquor including the important impurity para-toluic acid. This precipitation will cause the content of impurities, including para-toluic acid, in the PTA to increase. The consequence is either the product being out of specification or an increase in operating cost due to an operational change required to maintain product quality.

U.S. Pat. No. 5,583,254 generally discloses using an inert gas containing steam as an alternative means of creating the pressure driving force, but does not disclose any concentrations of steam to use. Additionally, steam has a commercial value and therefore would be an additional operating cost without recycling the gas containing steam. The problem with recycling the gas containing the steam is that some of the impurities, including para-toluic acid, are volatile in steam and hence the steam leaving the filter would be contaminated in these impurities and would contaminate the cake if directly recycled. U.S. Pat. No. 5,583,254 generally discloses that the gas can be treated and reintroduced, but does not disclose any methods for achieving that result. The consequence of these combined problems is either the product being out of specification or an increase in operating cost due to an operational change required to maintain the product quality.

Therefore, there exists a need to further i) minimize the impurities, including para-toulic acid, in the production of a pure carboxylic acid, for example pure terephthalic acid, and ii) reduce operating costs in maintaining product quality.

SUMMARY OF THE INVENTION

In accordance with the present invention, a method has been found to filter an aqueous slurry containing pure carboxylic acid without increasing the precipitation of impurities from the mother liquor and contaminating the product pure carboxylic acid or increasing the operating cost of the process. The present invention can be characterized by a process for production of pure terephthalic acid comprising: a) removing a mother liquor from a terephthalic acid through a filter with a gas, wherein the gas comprises steam at a concentration in a range of from about 50 weight % to about 99.9 weight % of the total gas; b) purifying the gas; and c) recycling the gas purified in step (b) back to step (a).

DETAILED DESCRIPTION

Figure 1:
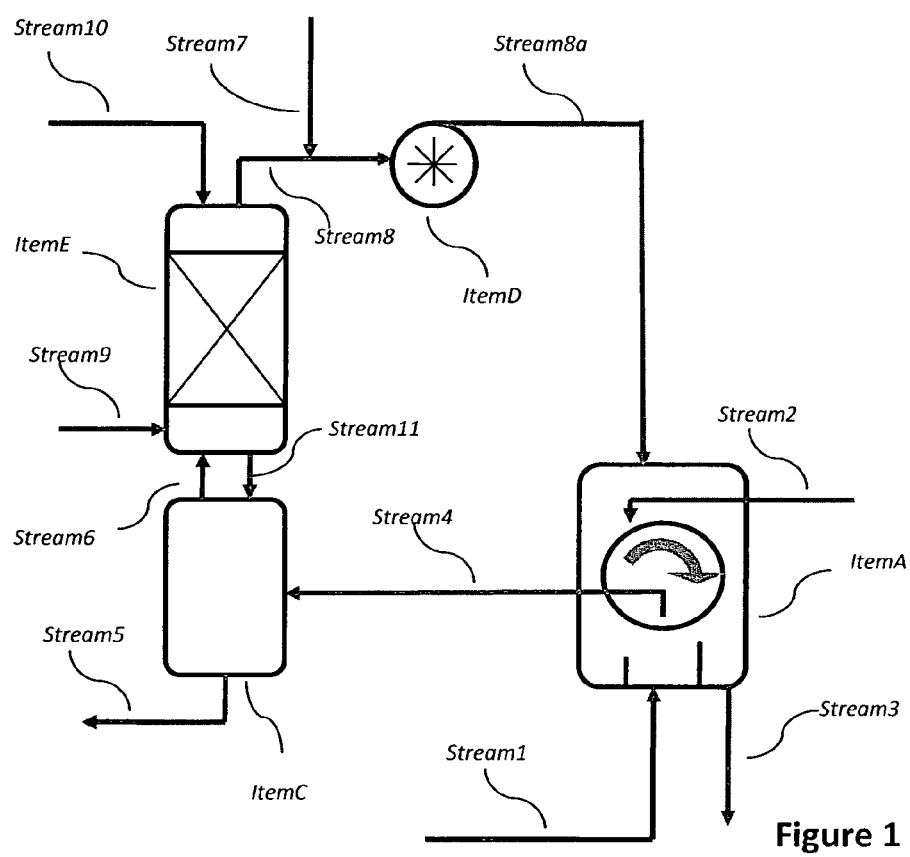
FIG. 1 is a schematic process diagram which illustrates one embodiment of the invention in which terephthalic acid is separated from a mother liquor via pressurized gas and a filter, and then the pressurized gas is purified and recycled.

The present invention can be characterized by a process for production of pure terephthalic acid comprising: a) removing a mother liquor from a terephthalic acid slurry through a filter with a gas, wherein the gas comprises steam at a concentration in a range of from about 50 weight % to about 99.9 weight % of the total gas; b) purifying the gas; and c) recycling the gas purified in step (b) back to step (a). Optionally, the terephthalic acid slurry can be contacted with the filter medium prior to step (a).

Another embodiment of the present invention can be characterized by a process for production of pure terephthalic acid comprising: (a) oxidizing a paraxylene to produce a crude terephthalic acid; (b) purifying the crude terephthalic acid to form a slurry comprising pure terephthalic acid; (c) contacting the mother liquor with a filter; (d) removing the mother liquor from the pure terephthalic acid through the filter with a gas, wherein the gas comprises steam at a concentration in a range of from about 50 weight % to about 99.9 weight % of the total gas; (e) purifying the gas in a gas-liquid contacting device; and (f) recycling the gas purified in step (e) back to step (d).

The following can be included in all embodiments of the present invention. The gas can comprise steam at a concentration in a range of from about 80 weight % to about 99 weight % of the total gas, for example about 80 weight % to about 95 weight % or about 85 weight % to about 95 weight %. The steam can be at a temperature in the range of from about 90° C. to about 210° C., for example in the range of from about 130° C. to about 180° C. The gas can further comprise a non-condensable gas. A non-condensable gas can be a gas wherein at least part of the gas does not condense at any of the process conditions and does not react with any other component or contaminant in the system. For example a non-condensable gas can comprise at least one member selected from the group consisting of nitrogen, oxygen, carbon dioxide, argon or mixtures thereof, such as air, spent air or vent gas recycled from the oxidation stage of the process. The purifying step (step (b) or step (e) above) can be in a gas-liquid separation or contact device, for example the gas-liquid separation or contact device can be a scrubber. The gas can be a pressurized gas. The gas can be at a pressure on the low pressure side of the filter in the range of from about 0.5 bara to about 19 bara, for example in the range of from about 2 bara to about 8 bara or from about 4 bara to about 6 bara. The pressure drop across the filter can be in the range of from about 0.1 bara to about 2.0 bara, for example from about 0.25 bara to about 1.0 bara. The filter can be a rotary drum filter, a single compartment drum filter, a belt filter or similar separation device; for example, the filter can be a rotary drum filter with at least one filter cell and at least one wash zone. For example, the rotary drum filter can have about 10 to about 50 individual filter cells or about 18 to about 48 individual filter cells.

The present invention may be better understood by reference to FIGS. 1, 2, 3 and 4 which illustrate terephthalic acid being separated from a mother liquor via pressurized gas and a filter, wherein the pressurized gas is purified and recycled.

Referring to FIG. 1, a feed Stream 1 to a filter Item A can comprise a mother liquor and terephthalic acid. For example, but not limited to, the composition of feed Stream 1 can comprise 1 wt %-50 wt % terephthalic acid and 99 wt %-50 wt % water. The feed Stream 1 can come from pure plant crystallizers through a feed vessel. Wash water to the filter can be supplied via Stream 2. The cake of pure terephthalic acid leaves the filter by Stream 3. The resultant filtrate and pressurized gas leave the filter by Stream 4 and can be directed to a gas-liquid separator Item C. A liquid filtrate stream leaves the gas-liquid separator by Stream 5 to effluent treatment and the pressurized gas leaves the gas-liquid separator by Stream 6. The pressurized gas in Stream 6 can be directed to a gas-liquid contact device Item E wherein hot clean water can be introduce by Stream 10 and make-up steam can be introduced by Stream 9. Stream 11 is the liquid leaving the gas-liquid contact device and Stream 8 is the pressurized gas leaving the gas-liquid contact device to be recycled to the filter Item A. Stream 7 can be a make-up of non-condensable inert gas into Stream 8. Additionally, Item D can be a blower or compressor in Stream 8 resulting in Stream 8a going to filter Item A. The location or order of Items C, D and E could be varied depending on the type of device and pressure of the gas at various stages of the gas recycle system.

Figure 2:
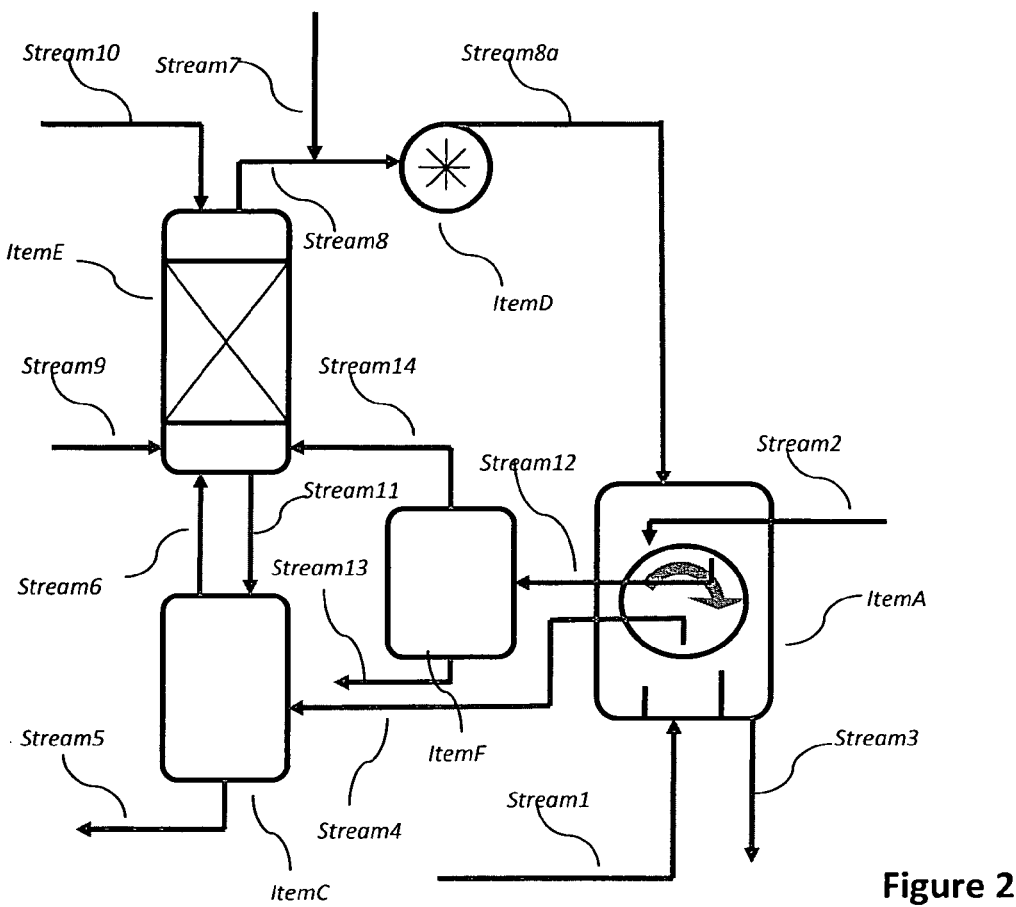
FIG. 2 is a schematic diagram of an alternative embodiment of the invention.

FIG. 2 illustrates an alternative configuration to FIG. 1 wherein some of the liquors collected from the wash stage of the filter are collected separately from the rest of the mother liquor and other filtrate. This can include a segregated filter with individual filter cells. Stream 12 includes the separately collected liquors and optionally some pressurized gas going to a second gas-liquid separator Item F. Stream 13 can be the liquid filtrate going to effluent treatment and Stream 14 can be the optional pressurized gas going to Item E if the pressurized gas is collected with the wash filtrate.

Figure 3:
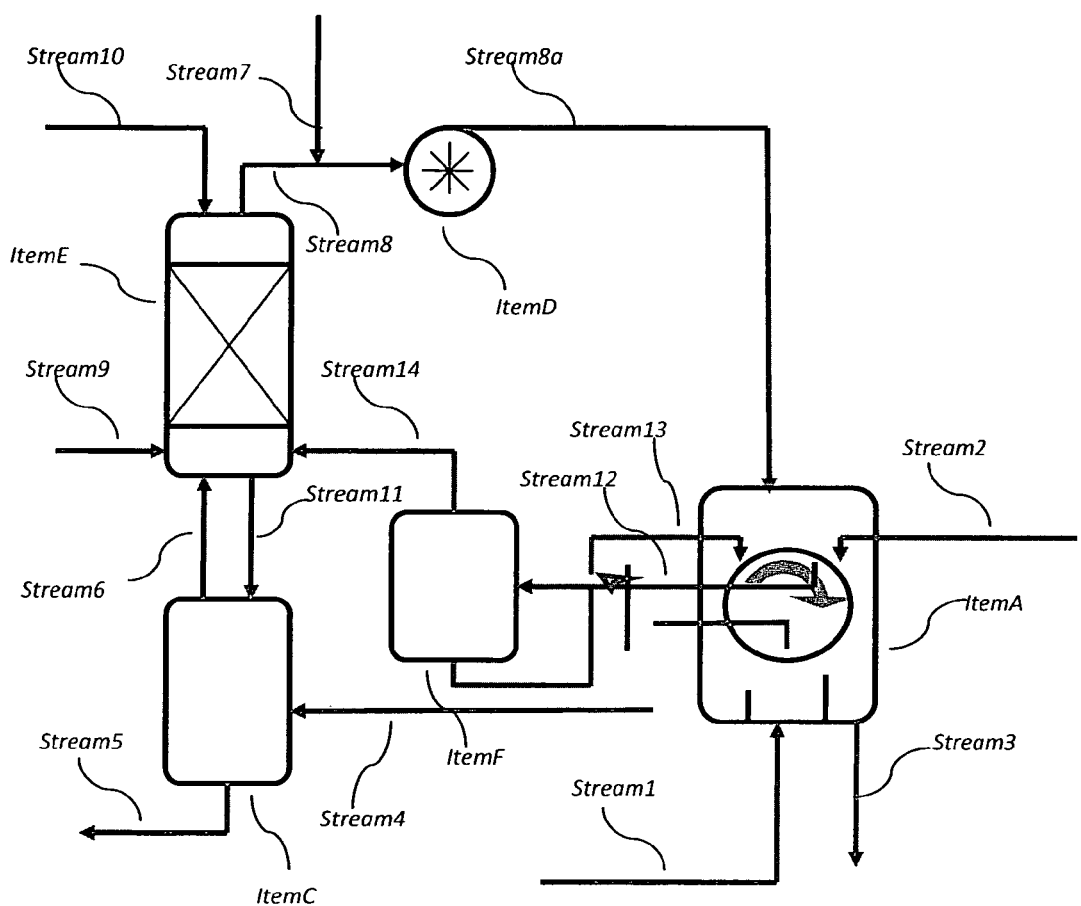
FIG. 3 is a schematic diagram of another alternative embodiment of the invention.

FIG. 3 illustrates an alternative configuration to FIG. 2 wherein the liquid filtrate from Item F, Stream 13, can be redirect to the filter Item A and used as an initial wash step and a second wash of clean water can be applied later during the filter cycle.

Figure 4:
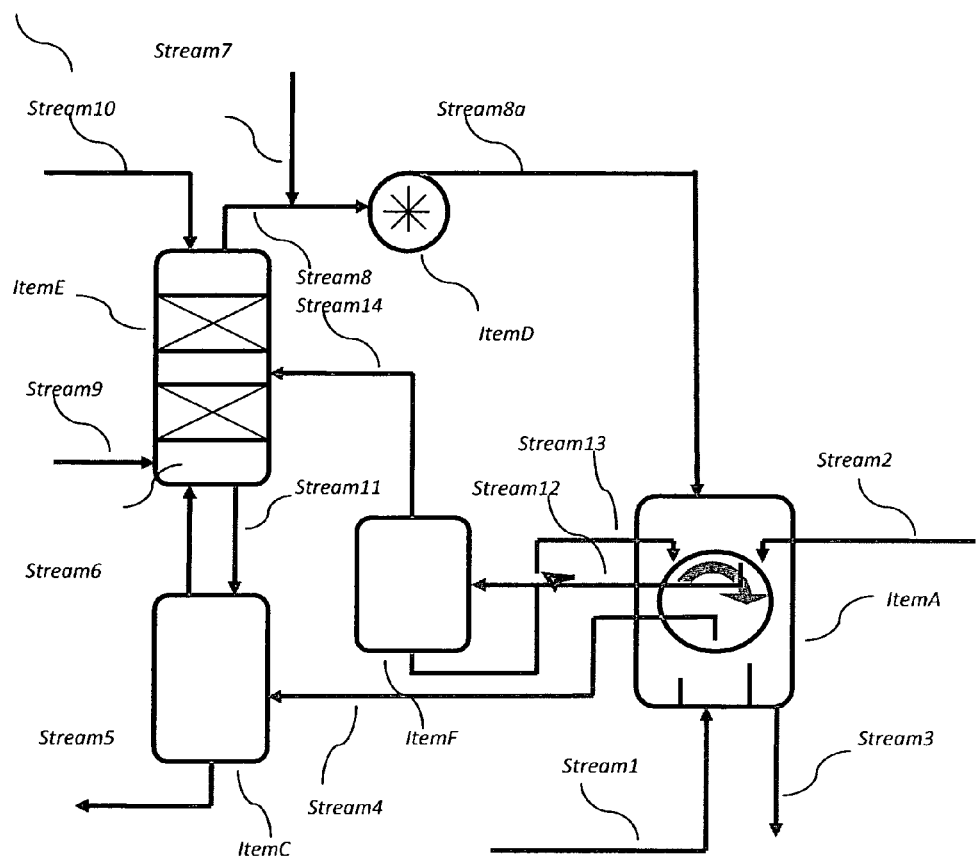
FIG. 4 is a schematic diagram of another alternative embodiment of the invention.

FIG. 4 illustrates an alternative configuration to FIGS. 2-3 wherein Streams 12 and 14 contain pressurized gas flow requiring Item E to contain at least two beds.

The present invention can use many different types of continuous filters. For example, all types of rotary drum filters and belt filters that use either vacuum or gas pressure to create the driving force for filtration can be used in the invention. Rotary drum filters are generally described in section 18-96 to 18-98 of "Perry's Chemical Engineers' Handbook" by Robert H. Perry and Don W. Green, Seventh Edition. Rotary drum filters can include single compartment drum filters such as the Bird Young Filter or rotary drum filters containing multiple compartments and drainage pipes. Single compartment drum filters typically collect all the filtrate and gas passing through the filter cloth and discharge it through a single discharge pipe. This type of filter can be used in the example given by FIG. 1. Additionally, filtrate collection pans can be included within the single compartment drum filter to separately collect liquors passing through the cloth at a particular point in the cycle. This would allow some of the liquors to be segregated. This type of filter can be used in the examples given by FIGS. 2, 3 and 4. Alternatively, a rotary drum filter with multiple drainage pipes separately collecting the liquors and gasses passing through different parts of the filter can be used in the invention. A control plate or filter control valve can be used to direct the filtrate and gases from different parts of the filter to different filtrate receivers. This type of filter can be used in the examples given by FIGS. 2, 3 and 4.

The following examples further illustrate the present invention.

Comparative Example 1

Figure 5:
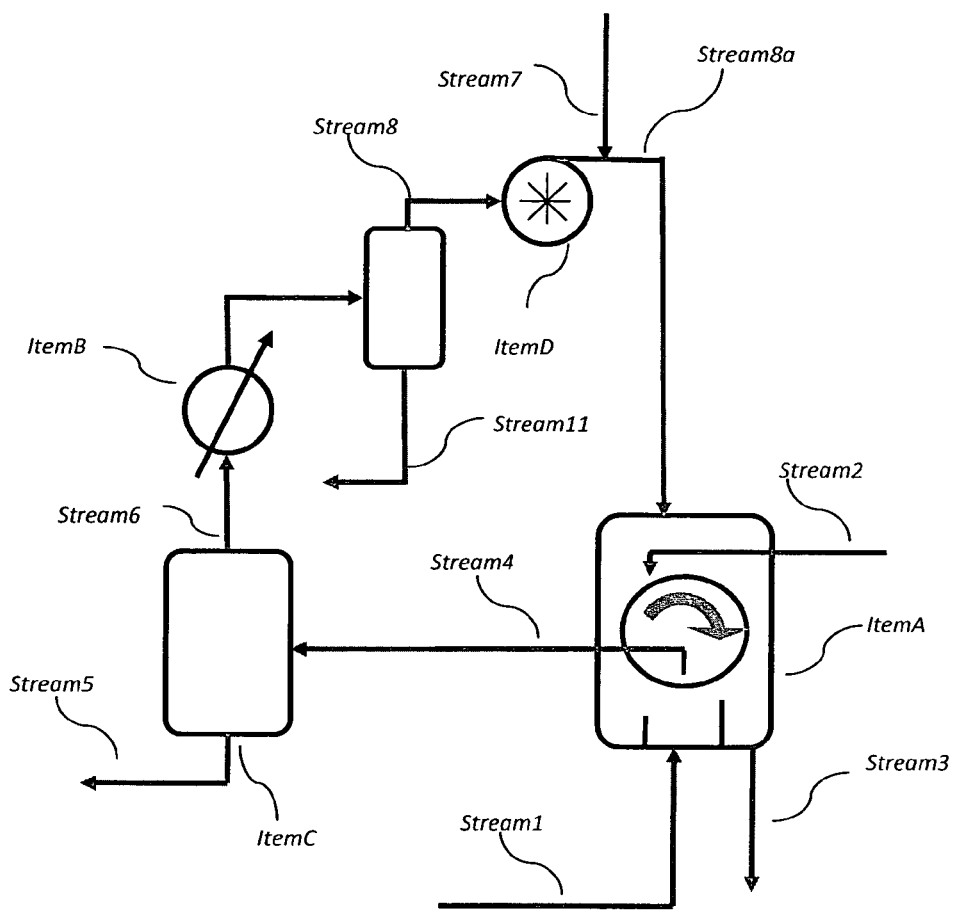
FIG. 5 is a schematic diagram of related art.

An Aspen simulation was run using the configuration of FIG. 5 where Item B is a condenser and the other streams and items are as described above. The conditions and results are in Table 1 below.

TABLE 1

| | |
|---|---|
| Stream 8-Gas Composition (% v/v) | 99% Nitrogen/1% Steam |
| Stream 8-Paratoluic Acid Concentration | <0.005 w/w |
| Item A Temperature | 49° C. |
| Item A Pressure | 5 Bara |
| Pressure Drop across filtercake and filter medium-Item A | 0.5 Bar |
| Stream 1-Paratoluic Acid Concentration (total sample basis) | 1221 ppm |
| Stream 3-Paratoluic Acid Concentration (total sample basis) | 135 ppm |

Example 2

An Aspen simulation was run using the configuration of FIG. 1 as described above. The conditions and results are in Table 2 below.

TABLE 2

| | |
|---|---|
| Stream 8-Gas Composition (% v/v) | 10% Nitrogen/90% Steam |
| Stream 8-Paratoluic Acid Concentration | <0.005 w/w |
| Item A Temperature | 148° C. |
| Item A Pressure | 5 Bara |
| Pressure Drop across filtercake/medium-Item A | 0.5 Bar |
| Stream 1-Paratoluic Acid Concentration (total sample basis) | 1221 ppm |
| Stream 3-Paratoluic Acid Concentration (total sample basis) | 129 ppm |

As can be seen there is a reduction of paratoluic acid in Stream 3 between Comparative Example 1 and Example 2. This reduction has significant commercial effects on the value of pure terephthalic acid.

While the invention has been described in conjunction with specific embodiments thereof, it is evident that the many alternatives, modifications, and variations will be apparent to those skilled in the art in light of the foregoing description. Accordingly, the invention is intended to embrace all such alternatives, modifications and variations as fall within the spirit and scope of the claims.

What is claimed is:

1. A process for production of pure terephthalic acid comprising:
    (a) removing a mother liquor from a purified terephthalic acid through a filter with a gas, wherein the gas comprises steam at a concentration in a range of from 85 weight % to 95 weight % of the total gas;
    (b) purifying the gas to remove volatile impurities, wherein the purifying is in a gas-liquid contact device and wherein said gas-liquid contact device is a scrubber; and
    (c) recycling the gas purified in step (b) back to step (a).

2. The process of claim 1 wherein the steam is at a temperature in the range of from 90° C. to 210° C.

3. The process of claim 1 wherein the steam is at a temperature in the range of from 130° C. to 180° C.

4. The process of claim 1 wherein the gas further comprises a non-condensable gas.

5. The process of claim 4 wherein the non-condensable gas it at least one member selected from the group consisting of nitrogen, oxygen, carbon dioxide, argon and mixtures thereof.

6. The process of claim 1 wherein the prior to step (a) the mother liquor comprising terephthalic acid is contacted with the filter medium.

7. The process of claim 1 wherein the gas is a pressurized gas.

8. The process of claim 1 wherein the gas is at a pressure in the range of from 0.5 bara to 19 bara, wherein the pressure is measured at a low pressure side of the filter.

9. The process of claim 1 wherein the gas is at a pressure in the range of from 2 bara to 8 bara, wherein the pressure is measured at a low pressure side of the filter.

10. The process of claim 1 wherein the gas is at a pressure in the range of from 4 bara to 6 bara, wherein the pressure is measured at a low pressure side of the filter.

11. The process of claim 1 wherein the filter is selected from the group consisting of a rotary drum filter, a single compartment drum filter, and a belt filter.

12. The process of claim 1 wherein the filter is a rotary drum filter.

13. The process of claim 12 wherein the rotary drum filter has at least one filter cell and at least one wash zone.

14. A process for production of pure terephthalic acid comprising:
    (a) oxidizing a paraxylene to produce a crude terephthalic acid;
    (b) purifying the crude terephthalic acid to form a mother liquor comprising pure terephthalic acid;
    (c) contacting the mother liquor with a filter;
    (d) removing the mother liquor from the pure terephthalic acid through the filter with a gas, wherein the gas comprises at steam at a concentration in a range of from 85 weight % to 95 weight % of the total gas;
    (e) purifying the gas to remove volatile impurities in a gas-liquid separation device wherein the purifying of step is in a gas-liquid contact device and wherein said gas-liquid contact device is a scrubber; and
    (f) recycling the gas purifying in step (e) back to step (d).

15. The process of claim 14 wherein the steam is at a temperature in the range of from 90° C. to 210° C.

16. The process of claim 14 wherein the steam is at a temperature in the range of from 130° C. to 180° C.

17. The process of claim 14 wherein the gas further comprises a non-condensable gas.

18. The process of claim 17 wherein the non-condensable gas is at least one member selected from the group consisting of nitrogen, oxygen, carbon dioxide, argon and mixtures thereof.

19. The process of claim 14 wherein the gas is a pressurized gas.

20. The process of claim 14 wherein the gas is at a pressure in the range of from 0.5 bara to 19 bara, wherein the pressure is measured at a low pressure side of the filter.

21. The process of claim 14 wherein the gas is at a pressure in the range of from 2 bara to 8 bara, wherein the pressure is measured at a low pressure side of the filter.

22. The process of claim 14 wherein the gas is at a pressure in the range of from 4 bara to 6 bara, wherein the pressure is measured at a low pressure side of the filter.

23. The process of claim 14 wherein the filter is selected from the group consisting of a rotary drum filter, a single compartment drum filter and a belt filter.

24. The process of claim 14 wherein the filter is a rotary drum filter.

25. The process of claim 24 wherein the rotary drum filter has at least one filter cell and at least one wash zone.

* * * * *

UNITED STATES PATENT AND TRADEMARK OFFICE
CERTIFICATE OF CORRECTION

PATENT NO.        : 9,199,905 B2
APPLICATION NO.   : 13/126640
DATED             : December 1, 2015
INVENTOR(S)       : Christopher H. Jackson et al.

It is certified that error appears in the above-identified patent and that said Letters Patent is hereby corrected as shown below:

Title page, item 75, line 6, "Alan MacPeherson Ure" should read --Alan MacPherson Ure--.

In the Claims

Claim 5, col. 5, lines 42-43, "gas it at least one member" should read --gas is at least one member--.

Signed and Sealed this
Fourteenth Day of June, 2016

Michelle K. Lee
*Director of the United States Patent and Trademark Office*